United States Patent [19]

Tamai et al.

[11] Patent Number: 4,507,232

[45] Date of Patent: Mar. 26, 1985

[54] PEPTIDE DERIVATIVES

[75] Inventors: Masaharu Tamai, Hasuda; Takashi Adachi, Kuki; Kiyoshi Oguma, Gyoda; Kazunori Hanada; Sadafumi Omura, both of Ageo; Nobuhiko Katunuma, Tokushima, all of Japan

[73] Assignee: Taisho Pharmaceutical Co., Ltd., Tokyo, Japan

[21] Appl. No.: 562,439

[22] Filed: Dec. 16, 1983

[30] Foreign Application Priority Data

Dec. 21, 1982 [JP] Japan .................................. 57-224684

[51] Int. Cl.$^3$ ........................................... C07C 103/52
[52] U.S. Cl. ........................................... 260/112.5 R
[58] Field of Search ................................. 260/112.5 R

[56] References Cited

PUBLICATIONS

Chem. Pharm. Bull. 30 (11) 4060–4068 (1982).

The Journal of Biological Chem. 244, No. 10, (1969), 2693–2709.
Journal of Clinical Microbiology (1982), 452–457, vol. 16.
J. Biochem. 93, 1129–1135 (1983).

*Primary Examiner*—Delbert R. Phillips
*Attorney, Agent, or Firm*—Frishauf, Holtz, Goodman & Woodward

[57] ABSTRACT

This invention is directed to novel peptide derivatives. Said peptide derivatives are useful as a substrate for the activity assay of enzymes of the group EC 3. 4. 22, for example, cathepsin L, cathepsin B and cathepsin H. Said peptide derivatives which contain L-methionine radical are prepared according to the methods conventional in peptide chemistry. As typical examples are mentioned D-leucyl-L-tyrosyl-L-methionine-β-naphthylamide formate, β-alanyl-L-tyrosyl-L-methionine-β-naphthylamide formate and succinyl-L-tyrosyl-L-methionine-p-nitroanilide.

6 Claims, No Drawings

PEPTIDE DERIVATIVES

BACKGROUND OF THE INVENTION

1. Field of the Invention

The present invention relates to novel peptide derivatives which are used as substrates for measuring the protease activities.

More particularly, this invention is concerned with peptide derivatives useful as color-developing or fluorescent substrates employed for measuring the activity of cysteine proteases in which a thiol group is essential for the exertion of the activity.

Enzymes of the group EC 3. 4. 22 are known to be cysteine proteases in which a thiol group is essential for the exertion of the activity. These enzymes are present in mammalian tissues such as muscles and liver and play an important physiological role. Therefore, measurement of the activity for these enzymes has a significance for elucidating many physiological actions in mammal tissues and is applicable to the diagnosis of diseases.

2. Description of the Prior Art

Activities of enzymes of the group EC 3. 4. 22, for example, cathepsin B [EC 3. 4. 22.1], cathepsin L [EC 3. 4. 22.-] and cathepsin H [EC 3. 44. 22.-] have been assayed with BANA ($\alpha$-N-benzoyl-DL-arginine-2-naphthylamide) as a substrate. BANA, however, is of a lower sensitivity for enzymes of the group EC 3. 4. 22, and it was difficult to effect the assay with this substrate when the specimen contained only a small amount of the enzyme. Particularly for muscle specimens which contain a very small amount of the enzyme substrates of high sensitivity are desired.

SUMMARY OF THE INVENTION

It is therefore an object of the present invention to provide substrates which enable the assay of enzymes of the group EC 3. 4. 22 by simple procedures and at a high sensitivity.

According to the invention, there are provided peptide derivatives having the general formula:

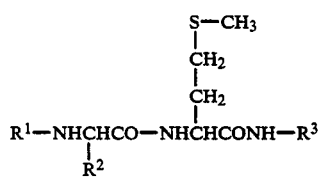

wherein $R^1$ represents an aliphatic acyl group containing 2-5 carbon atoms substituted with one or two groups selected from the group consisting of methyl, amino, carboxyl, hydroxyl and benzyloxy groups, a tertiary butoxycarbonyl group, an aminobenzoyl group or a hydrogen atom, $R^2$ represents a 2-methylpropyl, 1-methylpropyl, p-hydroxybenzyl, p-methoxybenzyl, benzyl or 3-guanidylpropyl group, and $R^3$ represents a naphthyl, methylcoumaryl or nitrophenyl group and pharmacologically acceptable acid addition salts thereof.

Further according to the invention, there are provided peptide derivatives of the above-mentioned general formula [I] wherein $R^1$ is a succinyl group, a leucyl group or a $\beta$-alanyl group, $R^2$ is a p-hydroxybenzyl group and $R^3$ is a naphthyl group or a p-nitrophenyl group.

Furthermore according to the invention, there are provided D-leucyl-L-tyrosyl-L-methionine-$\beta$-naphthylamide, $\beta$-alanyl-L-tyrosyl-L-methionine-$\beta$-naphthylamide, glycoloyl-L-tyrosyl-L-methionine-$\beta$-naphthylamide, succinyl-L-tyrosyl-L-methionine-$\beta$-naphthylamide and succinyl-L-tyrosyl-L-methionine-p-nitroanilide.

DETAILED DESCRIPTION OF THE INVENTION

Extensive investigations were made by us to find substrates which made simple and sensitive measurement available for the activity of enzymes of the group EC 3. 4. 22 present in mammalian tissues. We have now achieved synthesis of L-methione-containing peptide derivatives and found that the derivatives can be a color-developing or fluorescent substrate which enables a simple and sensitive assay of enzymes of the group EC 3. 4. 22.

The present invention is directed to peptide derivatives having the above-mentioned general formula [I]. The peptide derivatives [I] are hydrolyzed by the action of an enzyme of the group EC 3. 4. 22 to release a color-forming or fluorescent substance $R^3H$. By photometrically measuring the concentration of the substance activity of said enzyme can be determined.

The above hydrolysis reaction are so sensitive that highly sensitive assay of the above-mentioned enzymes is feasible with the peptide derivatives [I].

Particularly preferred of the peptide derivatives [I] are compounds wherein $R^1$ is a succinyl, leucyl or $\beta$-alanyl group, $R^2$ is p-hydroxybenzyl group and $R^3$ is a naphthyl or p-nitrophenyl group.

More preferable of the peptide derivatives [I] are D-leucyl-L-tyrosyl-L-methionine-$\beta$-naphthylamide, $\beta$-alanyl-L-tyrosyl-L-methionine-$\beta$-naphthylamide, glycoloyl-L-tyrosyl-L-methionine-$\beta$-naphthylamide, succinyl-L-tyrosyl-L-methionine-$\beta$-naphthylamide and succinyl-L-tyrosyl-L-methionine-p-nitroanilide.

The peptide derivatives [I] of the invention are prepared by the methods conventionally employed in peptide chemistry as shown below.

METHOD A (1) Method which comprises condensing a compound having the general formula

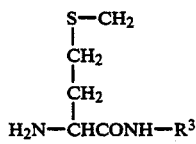

wherein $R^3$ has the same meaning as defined above with a compound having the general formula

wherein $R^2$ has the same meaning as defined above and $R^4$ is the same as the $R^1$ defined above or represents a protecting group conventionally employed in peptide chemistry in the presence of a condensing agent such as N,N'-dicyclohexylcarbodiimide or 1-ethyl-3-(3'-dimethylaminopropyl)carbodiimide.

The above-mentioned condensation reaction is preferably carried out by subjecting a mixture of the compound [II], the compound [III] and the condensing agent in a solvent such as tetrahydrofuran, dimethylformamide, chloroform, ethyl acetate or dichloromethane to stirring at room temperature or in an ice-bath for 3 hours to overnight.

(2) Mixed acid anhydride method which comprises converting the compound [III] to a mixed acid anhydride with a chloroformic acid ester such as isobutyroxycarbonyl chloride or ethyloxycarbonyl chloride and then reacting the mixed acid anhydride with the compound [II].

In the above method, the step for preparing a mixed acid anhydride is carried out by reacting the compound [III] and the acid chloride in the presence of a solvent such as tetrahydrofuran, ethyl acetate, dimethylformamide or dimethyl sulfoxide at a temperature of $-15°$ to $-10°$ C. for a period of 2 to 20 min.

The reaction of the mixed acid anhydride with the compound [II] is preferably carried out in the presence of a solvent such as tetrahydrofuran, ethyl acetate, chloroform, dimethyl sulfoxide or dimethylformamide at a temperature of $-15°$ to $-10°$ C. for 1 hour and then at room temperature for 1 hour to overnight.

(3) Method which comprises reacting the compound [III] with a hydroxy compound such as N-hydroxysuccinimide or p-nitrophenol to prepare an active ester and then reacting the active ester with the compound [II].

The step for preparing an active ester in the above method is carried out by reacting the compound [III] and the hydroxy compound in the presence of a solvent such as tetrahydrofuran, dioxane, chloroform, dimethylformamide, dichloromethane or ethyl acetate while being cooled in an ice-bath or at room temperature for 2 hours to overnight.

The step for reacting the active ester and the compound [II] is carried out in a solvent under the same conditions as in the aforementioned step.

When $R^4$ in the compounds [III] in the above-described method A is a protecting group conventionally employed in peptide chemistry, typical examples are benzyloxycarbonyl, p-methoxybenzyloxycarbonyl, tert.-butoxycarbonyl, tert.-amyloxycarbonyl, o-nitrophenylsulfenyl, trityl and like groups.

The $R^4$ in the compounds [III] wherein it is a protecting group conventionally employed in peptide chemistry can be removed by means of the cleavage conventional in peptide chemistry to produce the compounds [I] wherein $R^1$ is hydrogen atom. For example, when the $R^4$ is tert.-butoxycarbonyl group the removal can be accomplished by an acid treatment, and when the $R^4$ is benzyloxycarbonyl or p-methoxybenzyloxycarbonyl group, it can be removed by a catalytic reduction or an acid treatment.

METHOD B (1) Method which comprises combining a peptide derivative [I] wherein $R^1$ is hydrogen atom with a compound having the general formula $$R^5-OH \qquad [IV]$$

wherein $R^5$ is the same as defined for $R^1$ excluding a hydrogen atom or a compound [IV] with an appropriate protecting group attached by an analogous method to the above-mentioned Method A (1)–(3), and if a protecting group is present, removing the protecting group by an appropriate method to prepare the peptide derivative [I] wherein $R^1$ is other group as defined above than a hydrogen atom.

(2) Method which comprises reacting a peptide derivative [I] wherein $R^1$ is a hydrogen atom with a dicarboxylic anhydride such as malonic, succinic or glutaric anhydride to form a peptide derivative [I] wherein $R^1$ is other group as defined above than a hydrogen atom.

The above-mentioned method is carried out by reacting the peptide derivative [I] wherein $R^1$ is a hydrogen atom and the dicarboxylic anhydride in the presence of a solvent such as ethylether, acetonitrile, tetrahydrofuran or chloroform with cooling with ice or at room temperature for 2 hours to overnight.

METHOD C

Method which comprises reacting a compound having the general formula

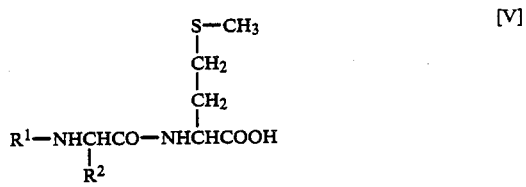

wherein $R^1$ and $R^2$ are the same as defined above and to which an appropriate protecting group is attached, if necessary with a compound having the general formula

wherein $R^3$ has the same meaning as above by a method analogous to the above-described method A (2) or (3), and if the protecting group is present, removing it by an appropriate method to give the peptide derivatives [I].

In the above-mentioned method, the same protecting groups as described in the method A may be employed in case where the compounds [V] are attached with a protecting group.

The compounds [II]–[VI] employed in the methods A–C are known or similar to known compounds and may be prepared by conventional methods.

The peptide derivatives of the present invention may be converted to pharmacologically acceptable acid addition salts thereof by the conventional method if desired. As examples of the acid forming the acid addition salts are mentioned formic, trifluoroacetic, hydrochloric and sulfuric acids.

In employing the peptide derivatives [I] of the invention as a substrate for the proteases of the group EC 3. 4. 22, the enzyme is incubated with a predetermined amount of the peptide derivative [I] in an appropriate buffer solution at a predetermined temperature for a predetermined period of time. By measuring β-naphthylamine, 4-methyl-7-aminocoumarin or p-nitroaniline thus liberated, the enzymatic activity can be determined at a high sensitivity.

Various methods have heretofore been known for the measurement of β-naphthylamine, 4-methyl-7-aminocoumarin or p-nitroaniline. When β-naphthylamine is liberated, an excitation is made around 355 nm, and intensity of the fluorescence around 410 nm is measured with a fluorometer, or color is developed with Fast Garnet GBC Salt, and absorbance around 520 nm is measured with a spectrophotometer. For 4-methyl-7-aminocoumarin, an excitation is made around 380 nm, and intensity of the fluorescence at 440 nm is measured with a fluorometer. For p-nitroaniline, measurement of the absorbance around 410 nm is preferable because it is simple and sensitive.

The peptide derivatives [I] of the invention is useful as a color-developing or fluorescent substrate for the assay of cysteine proteases in which a thiol group is essential for the exertion of the activity.

The invention will be described below in embodiment with reference to tests illustrating that the peptide derivatives [I] of the invention are highly sensitive substrates for proteases as well as examples of the preparation of the peptide derivatives [I].

TEST EXAMPLE 1

Reactions were made respectively with pure preparations of cathepsins B, L and H of rat livers according to the method of A. J. Barrett (Analytical Biochemistry vol. 47, pp. 280–293 (1972)) except that various peptide derivatives of the general formula [I] were used in place of N-benzoyl-alginine-β-naphthylamide, and the reactions were carried out for 20 min. at pH 5.0.

To 2 ml. of a mixture containing ethylenediaminetetraacetic acid (1 mM), cysteine (2 mM), acetate buffer (pH 5.0, 0.1M) and an enzyme preincubated at 40° C. for 5 min. was added 50 μl. of a dimethyl sulfoxide solution of a peptide derivative of the general formula [I] (80 mM). The resulting mixture was incubated at 37° C. for 20 min. To the reaction mixture was added 2 ml. of a solution containing p-chlormercuribenzoic acid (5 mM), ethylenediaminetetraacetic acid (25 mM), Brij-35 (0.2%) and Fast Garnet GBC salt (250 μg./ml.) After several minutes was added 4 ml. of n-butanol. The mixture was vigorously shaken and centrifuged. The organic layer was separated, for which absorbance at 520 nm was measured.

When the liberated substance was β-naphthylamine, measurement was made according to the above-cited method of A. J. Barrett.

The liberated amount was determined for 4-methyl-7-aminocoumarin by exciting at 380 nm and measuring intensity of the fluorescence at 440 nm with a fluorometer, and for p-nitroaniline by measuring absorbance at 410 nm with a spectrophotometer.

Hydrolyzability of the peptide derivatives [I] with the above-cited cathepsins was expressed in terms of μmols of β-naphthylamine, 4-methyl-7-aminocoumarin or p-nitroaniline liberated in one minute per mg. of the enzyme. Results are shown in Table 1.

TABLE 1

| Compound No. | Hydrolyzability of substrates. | | |
|---|---|---|---|
| | Cathepsin L | Cathepsin B | Cathepsin H |
| 1 | 0.701 | 0.315 | 0.012 |
| 2 | 0.473 | 0.043 | 0.035 |
| 3 | 1.198 | 0.341 | 0.023 |
| 4 | 1.252 | 0.266 | 0.184 |
| 5 | 0.139 | 0.090 | 1.209 |
| 6 | 0.702 | 0.180 | 0.023 |
| 7 | 0.400 | 1.310 | 0.155 |
| 8 | 2.491 | 2.981 | 0.009 |
| 9 | 2.106 | 2.486 | 0 |
| 10 | 0.950 | 2.396 | 0.029 |
| 11 | 1.565 | 2.246 | 0 |
| 12 | 0.722 | 0.530 | 0 |
| 13 | 0.343 | 0.826 | 0 |
| 15 | 0.080 | 0.006 | 0 |

TABLE 1-continued

| Compound No. | Hydrolyzability of substrates. | | |
|---|---|---|---|
| | Cathepsin L | Cathepsin B | Cathepsin H |
| 17 | 1.637 | 1.120 | 0 |

Note.
Compound number is referred to by the example number in which the compound was prepared.

TEST EXAMPLE 2

The same procedures as those in Test Example 1 above were followed except that phosphate buffer (pH 6.0, 0.1M) was used in place of the acetate buff (pH 5.0, 0.1M) to determine hydrolyzability of the peptide derivatives [I]. Results are shown in Table 2.

TABLE 2

| Compound No. | Hydrolyzability of substrates. | | |
|---|---|---|---|
| | Cathepsin L | Cathepsin B | Cathepsin H |
| BANA | 0.117 | 0.669 | 1.884 |
| 8 | 7.583 | 1.246 | 0.020 |
| 9 | 7.582 | 1.901 | 0.026 |
| 17 | 5.107 | 1.925 | 0.068 |

EXAMPLE 1

To a solution of 1.0 g. of tert.-butoxycarbonyl-L-tyrosin, 0.98 g. of L-methionine-β-naphthylamide, 0.53 g. of 1-hydroxybenzotriazole and 0.39 g. of N-methylmorpholine in 80 ml. of tetrahydrofuran was added 0.75 g. of 1-ethyl-3-(3-dimethylaminopropyl)carbodiimide slowly with stirring and ice cooling. The mixture was stirred with ice cooling for 2 hours and at room temperature for additional 2 hours, followed by concentration under reduced pressure. To the concentrate were added 100 ml. of ethyl acetate and 80 ml. of water. The mixture was vigorously shaken, and the ethyl acetate layer was separated, which was successively washed with 10% citric acid solution, saturated aqueous sodium bicarbonate and saturated aqueous sodium chloride and then concentrated to dryness. The residue thus obtained was crystallized from ethyl acetate-n-hexane. There was obtained 1.31 g. of tert.-butoxycarbonyl-L-tyrosyl-L-methionine-β-naphthylamide. Yield 71%. m.p. 201°–202° C.

EXAMPLE 2

A solution of 523 mg. of tert.-butoxycarbonyl-L-tyrosyl-L-methionine-β-naphthylamide in 10 ml. of formic acid was stirred at room temperature for 3 hours and then concentrated under reduced pressure. The residue thus obtained was crystallized from ethyl acetate-n-hexane to give 447 mg. of L-tyrosyl-L-methionine-β-naphthylamine formate. Yield 95%. m.p. 175°–177° C.

EXAMPLE 3

A solution of 500 mg. of tert.-butoxycarbonyl-L-phenylalanyl-L-methionine-β-naphthylamide which had been prepared in the same way as in Example 1 from tert.-butoxycarbonyl-L-phenylalanine and L-methionine-β-naphthylamide in 10 ml. of formic acid was treated in the same way as in Example 2 to obtain 335 mg. of L-phenylalanyl-L-methionine-β-naphthylamide formate. Yield 83%. m.p. 142°–144° C.

EXAMPLE 4

A solution of 974 mg. of tert.-butoxycarbonyl-L-leucyl-L-methionine-β-naphthylamide which had been prepared in the same way as in Example 1 from tert.-butoxycarbonyl-L-leucine monohydrate and L-methionine-β-naphthylamide in 30 ml. of formic acid was treated in the same way as in Example 2 to obtain 675 mg. of L-leucyl-L-methionine-β-naphthylamide formate. Yield 78%. m.p. 118°–119° C.

EXAMPLE 5

A solution of 600 mg. of tert.-butoxycarbonyl-L-isoleucyl-L-methionine-β-naphthylamine which had been obtained in the same way as in Example 1 from tert.-butoxycarbonyl-L-isoleucine and L-methionine-β-naphthylamide in 20 ml. of formic acid was treated in the same way as in Example 2 to obtain 456 mg. of L-isoleucyl-L-methionine-β-naphthylamide formate. Yield 85.5%. m.p. 156°–157° C.

EXAMPLE 6

Into a solution of 250 mg. of tert.-butoxycarbonyl-L-tyrosyl-L-methionine-β-naphthylamide in a mixed solvent of methanol-ether-dichloromethane was bubbled diazomethane. The resulting mixture was allowed to stand overnight at room temperature, to which was then added acetic acid. The mixture was concentrated under reduced pressure, and the residue was crystallized from ethyl acetate-n-hexane. There was obtained 200 mg. of tert.-butoxycarbonyl-O-methyl-L-tyroxyl-L-methionine-β-naphthylamide, which was dissolved in 10 ml. of formic acid. The solution was treated in the same way as in Example 2 to obtain 148 mg. of O-methyl-L-tyrosyl-L-methionine-β-naphthylamide formate. Yield 82.2%. m.p. 135°–137° C.

EXAMPLE 7

To a solution of 250 mg. of tert.-butoxycarbonyl-$N^G$-nitro-L-arginyl-L-methionine-β-naphthylamide which had been prepared in the same way as in Example 1 from tert.-butoxycarbonyl-$N^G$-nitro-L-arginine and L-methionine-β-naphthylamide in 30 ml. of absolute methanol were added 200 mg. of palladium-on-carbon and 0.2 ml. of $BF_3$-ether. Into the mixture was bubbled hydrogen gas with stirring. When evolution of carbon dioxide was no longer observed, hydrogen gas was passed through for additional one hour (4–5 hours in total). The palladium-on-carbon was filtered off, and the filtrate was concentrated under reduced pressure. The residue thus obtained was purified by means of silica gel column chromatography. There was obtained 98 mg. of tert.-butoxycarbonyl-L-arginyl-L-methionine-β-naphthylamide. Yield 41%. m.p. 106°–107° C.

EXAMPLE 8

A solution of 250 mg. of tert.-butoxycarbonyl-D-leucyl-L-tyrosyl-L-methionine-β-naphthylamide which had been prepared in the same way as in Example 1 from L-tyrosyl-methionine-β-naphthylamide and tert.-butoxycarbonyl-D-leucine in 30 ml. of formic acid was treated in the same way as in Example 2 to obtain 200 mg. of D-leucyl-L-tyrosyl-L-methionine-β-naphthylamide formate. Yield 88%. m.p. 223°–225° C.

EXAMPLE 9

A solution of 400 mg. of tert.-butoxycarbonyl-β-alanyl-L-tyrosyl-L-methionine-β-naphthylamine prepared in the same way as in Example 1 from tert.-butoxycarbonyl-β-alanine and L-tyrosyl-L-methionine-β-naphthylamide in 50 ml. of formic acid was treated in the same way as in Example 2 to obtain 215 mg. of β-alanyl-L-tyrosyl-L-methionine-β-naphthylamide formate. Yield 60%. m.p. 188°–190° C.

EXAMPLE 10

The same procedures as in Example 1 were followed with 76 mg. of glycolic acid and 437 mg. of L-tyrosyl-L-methionine-β-naphthylamide followed by purification by silica gel column chromatography and subsequent crystallization from ethyl acetate-ether. There was obtained 218 mg. of glycoloyl-L-tyrosyl-L-methionine-β-naphthylamide. Yield 44%. m.p. 251°–253° C. (decomposed).

EXAMPLE 11

To a solution of 1.4 g. of L-tyrosyl-L-methionine-β-naphthylamide and 0.9 g. of triethylamine in 150 ml. of acetonitrile was dropwise added a solution of 0.36 g. of succinic anhydride in 80 ml. of acetonitrile with ice cooling and stirring. Stirring was continued for 30 min. with ice cooling and for additional 4 hours at room temperature. Then, the solvent was distilled off, and to the residue was added 50 ml. of water. The mixture was made acidic with 10% aqueous citric acid, followed by addition of ethyl acetate. The mixture was vigorously shaken, and the ethyl acetate layer was separated. The organic layer was dried over magnesium sulfate and then concentrated to dryness. Crude crystals thus obtained were recrystallized from methanol-water to obtain 1.34 g. of succinyl-L-tyrosyl-L-methionine-β-naphthylamide. Yield 83.2%. m.p. 220°–221° C.

EXAMPLE 12

The same procedures as in Example 1 were followed with 237 mg. of tert.-butoxycarbonyl-p-aminobenzoic acid and 437 mg. of L-tyrosyl-L-methionine-β-naphthylamide. The residue obtained was purified by means of silica gel column chromatography. There was obtained 400 mg. of tert.-butoxycarbonyl-p-aminobenzoyl-L-tyrosyl-L-methionine-β-naphthylamide, which was dissolved in 20 ml. of formic acid and then treated in the same way as in Example 2 to obtain 205 mg. of p-aminobenzoyl-L-tyrosyl-L-methionine-β-naphthylamide formate. Yield 55.8%. m.p. 235°–238° C. (decomposed).

EXAMPLE 13

A solution of 200 mg. of tert.-butoxycarbonyl-O-benzyl-D-seryl-L-tyrosyl-L-methionine-β-naphthylamide prepared in the same way as in Example 1 from tert.-butoxycarbonyl-O-benzyl-D-serine and L-tyrosine-L-methionine-β-naphthylamide in 10 ml. of trifluoroacetic acid was stirred at room temperature for 2 hours and then concentrated under reduced pressure. The residue thus obtained was crystallized from methanol-ethanol-n-hexane to obtain 165 mg. of O-benzyl-D-seryl-L-tyrosyl-L-methionine-β-naphthylamide trifluoroacetate. Yield 92.2%. m.p. 188°–190° C.

EXAMPLE 14

A solution of 400 mg. of tert.-butoxycarbonyl-L-methionine-4-methylcoumaryl-7-amide in 5 ml. of trifluoroacetic acid was stirred at room temperature for 20 min., and the trifluoroacetic acid was distilled off. To the oily substance thus obtained was added 30 ml. of ether, and precipitates formed were separated by filtration. A solution of the precipitates and 375 mg. of tert.-butoxycarbonyl-L-tyrosyl-N-hydroxysuccinimide ester in 10 ml. of DMF was stirred at room temperature for 10 hours. To the resulting solution were added 200 ml. of ethyl acetate and 150 ml. of saturated aqueous sodium chloride, and the mixture was vigorously shaken. The ethyl acetate layer was separated, successively washed with 1N aqueous hydrochloric acid, saturated aqueous sodium bicarbonate and saturated aqueous sodium chloride, dried over magnesium sulfate and concentrated to dryness. The residue thus obtained was crystallized from chloroform-n-hexane to obtain 300 mg. of tert.-butoxycarbonyl-L-tyrosyl-L-methionine-4-methylcoumaryl-7-amide. Yield 55.5%. m.p. 211°–212° C.

EXAMPLE 15

A solution of 220 mg. of tert.-butoxycarbonyl-L-tyrosyl-L-methionine-4-methylcoumaryl-7-amide in 2 ml. of trifluoroacetic acid was stirred at room temperature for 30 min., and the trifluoroacetic acid was distilled off. To the residue thus obtained was added 10 ml. of ether. White crystals, L-tyrosyl-L-methionine-4-methylcoumaryl-7-amide trifluoroacetate thus formed were separated by filtration. To a solution of the precipitates and 200 mg. of triethylamine in 3 ml. of acetonitrile and 3 ml. of tetrahydrofuran was dropwise added a solution of 46 mg. of succinic anhydride in 4 ml. of acetonitrile with ice cooling and stirring. The resulting mixture was stirred at room temperature for 3 hours and then allowed to stand overnight. The residue from distillation of the solvent was dissolved in 150 ml. of ethyl acetate. The ethyl acetate solution was successively washed with 1N aqueous hydrochloric acid and saturated aqueous sodium chloride, dried over magnesium sulfate and concentrated to dryness. The residue thus obtained was crystallized from methanol-ethyl acetate-petroleum ether to obtain 100 mg. of succinyl-L-tyrosyl-L-methionine-4-methylcoumaryl-7-amide. Yield 45%. m.p. 185°–186° C.

EXAMPLE 16

A solution of 1.17 g. of tert.-butoxycarbonyl-L-tyrosyl-N-succinimide ester and 0.759 g. of L-methionine-p-nitroanilide in 50 ml. of tetrahydrofuran was stirred at room temperature for 10 hours and then concentrated under reduced pressure. To the concentrate were added 150 ml. of ethyl acetate and 100 ml. of water, and the mixture was vigorously shaken. The ethyl acetate layer was separated by filtration and successively washed with 1N aqueous hydrochloric acid, saturated aqueous sodium bicarbonate and saturated aqueous sodium chloride, dried over magnesium sulfate and concentrated to dryness. The residue thus obtained was crystallized from ethyl acetate-n-hexane to obtain 1.17 g. of tert.-butoxycarbonyl-L-tyrosyl-L-methionine-p-nitroanilide. Yield 78%. m.p. 189°–190° C.

EXAMPLE 17

A solution of 1.07 g. of tert.-butoxycarbonyl-L-tyrosyl-L-methionine-p-nitroanilide in 8 ml. of trifluoroacetic acid was stirred at room temperature for 30 min., and the trifluoroacetic acid was then distilled off. To the residue thus obtained was added 70 ml. of ether to form white crystals of L-tyrosyl-L-methionine-p-nitroanilide trifluoroacetate, which were separated by filtration. To a solution of the precipitates and 0.610 g. of triethylamine in 100 ml. of acetonitrile was dropwise added a solution of 0.221 g. of succinic anhydride in 30 ml. of acetonitrile with ice cooling and stirring. After allowed to stand overnight, the solvent was distilled off, and the residue was dissolved in 200 ml. of ethyl acetate. The solution was washed with 10% aqueous citric acid, dried over magnesium sulfate and concentrated to dryness. The residue thus obtained was purified by silica gel column chromatography (chloroform: methanol = 10:1) and crystallized from dimethyl sulfoxide-water. There was obtained 0.15 g. of succinyl-L-tyrosyl-L-methionine-p-nitroanilide. Yield 47.7%. m.p. 152°–154° C.

What we claim is:

1. Peptide compounds having the formula

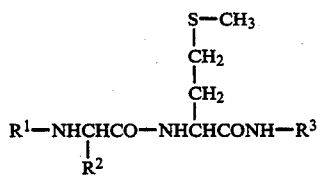

wherein $R^1$ is selected from the group consisting of a succinyl group, a leucyl group, and a β-alanyl group, $R^2$ is a p-hydroxybenzyl group, and $R^3$ is a naphthyl group, and pharmacologically acceptable acid addition salts thereof.

2. The peptide compound of claim 1, which is D-leucyl-L-tyrosyl-L-methionine-β-naphthylamide.

3. The peptide compound of claim 1, which is β-alanyl-L-tyrosyl-L-methionine-β-naphthylamide.

4. The peptide compound of claim 1, which is glycoloyl-L-tyrosyl-L-methionine-β-naphthylamide.

5. The peptide compound of claim 1, which is succinyl-L-tyrosyl-L-methionine-β-naphthylamide.

6. The peptide compound of claim 1, which is succinyl-L-tyrosyl-L-methionine-p-nitroanilide.

* * * * *